United States Patent [19]

Heinz et al.

[11] Patent Number: 4,901,339

[45] Date of Patent: Feb. 13, 1990

[54] STAND FOR AN X-RAY EXAMINATION APPARATUS COMPRISING A TELESCOPING COLUMN

[75] Inventors: Lothar Heinz, Neunkirchen; Thomas Schmitt, Forchheim, both of Fed. Rep. of Germany

[73] Assignee: Siemens Aktiengesellschaft, Berlin and Munich, Fed. Rep. of Germany

[21] Appl. No.: 216,202

[22] Filed: Jul. 7, 1988

[30] Foreign Application Priority Data

Jul. 23, 1987 [DE] Fed. Rep. of Germany ....... 8710117

[51] Int. Cl.$^4$ ............................................. H05G 1/02
[52] U.S. Cl. .................................... 378/197; 378/198; 248/332
[58] Field of Search ........................... 378/11, 194–198; 248/327, 332

[56] References Cited

U.S. PATENT DOCUMENTS

| 3,118,066 | 1/1964 | Thomas et al. | 378/197 |
| 3,175,085 | 3/1965 | Avery | 378/194 |
| 3,902,070 | 8/1975 | Amor, Jr. et al. | 378/194 |
| 4,041,320 | 8/1977 | Amor, Jr. et al. | 378/197 |

FOREIGN PATENT DOCUMENTS

| 531154 | 11/1957 | Belgium . | |
| 899228 | 10/1984 | Belgium . | |
| 831773 | 4/1952 | Fed. Rep. of Germany . | |
| 1466864 | 5/1969 | Fed. Rep. of Germany | 378/197 |
| 0916178 | 1/1963 | United Kingdom | 378/197 |
| 0969243 | 9/1964 | United Kingdom | 378/197 |

Primary Examiner—Janice A. Howell
Assistant Examiner—John C. Freeman
Attorney, Agent, or Firm—Hill, Van Santen, Steadman & Simpson

[57] ABSTRACT

The invention is directed to a stand for an x-ray examination apparatus comprising a telescoping column that, for example, guides an x-radiator adjustably in the direction of its longitudinal axis and comprises at least three tubular telescope parts joined inside one another, whereby the telescope parts are coupled such to one another that, given adjustment of the x-radiator, the same relative displacement occurs between respectively two telescope parts adjacent to one another and whereby respective stops are provided between telescope parts adjacent to one another. Adjustment devices are thereby provided with which the position of the telescope parts is adjustable such relative to one another in the direction of the longitudinal axis of the telescoping column that all stops take effect essentially simultaneously and the adjustment devices are fashioned and arranged such that they are actuatable without dismantling the telescoping column.

8 Claims, 2 Drawing Sheets

STAND FOR AN X-RAY EXAMINATION APPARATUS COMPRISING A TELESCOPING COLUMN

BACKGROUND OF THE INVENTION

The invention is directed to a stand for an x-ray examination apparatus having a telescoping column that guides a part of the x-ray examination apparatus, for example an x-radiator, adjustable in the direction of its longitudinal axis and comprises at least three tubular telescope parts joined inside one another, whereof one is stationary relative to the others, one carries the part of the x-ray examination apparatus and one is connected to means for adjusting the part, whereby the telescope parts are coupled such to one another that the same relative displacement respectively occurs between two neighboring telescoping parts upon adjustment of the part and whereby respective stop means for limiting the relative displacement are provided between telescope parts adjacent to one another.

Such a stand or support that is executed as a ceiling support having vertically directed telescoping column to which an x-radiator is attached in height-adjustable fashion is disclosed by U.S. Pat. No. 3,902,070. In the known stand or support, cables are provided as means for adjusting the x-radiator as well as for coupling the telescope parts to one another. Those cables that serve the purpose of coupling the telescope parts must thereby comprise such a length that, given complete extension or retraction of the telescoping column, all stop means provided for limiting the relative displacement between telescoping parts adjacent to one another take effect at essentially the same time since the cables coupling the telescope parts could otherwise tear given a jerky, complete extension or retraction of the telescoping column. In the course of mounting the known stand or support, the telescoping column must therefore usually be dismantled several times for correcting the lengths of the cables coupling the telescope parts until these are ultimately adapted such that all stop means act simultaneously. The same procedure that is involved, time-consuming and cost-intensive is required when individual cables must be replaced during maintenance or repair.

SUMMARY OF THE INVENTION

An object of the invention is to fashion a stand of the type described above such that assembly, maintenance and repair of the telescoping column are possible in a simple way.

In accord with the invention, this object is achieved in that adjustment means are provided with which the position of the telescope parts are adjustable relative to one another such in direction of the longitudinal axis of the telescoping column that all stop means take effect essentially simultaneously, and in that the adjustment means are fashioned and arranged such that they can be actuated without dismantling the telescoping column. As a consequence of the invention, thus, the telescoping column can be assembled without special measures in view of the coupling of the telescope parts during mounting of the stand or support, since the adjustment means that can be actuated without dismantling the telescoping column after assembly has been carried out make it possible to adjust the position of the telescope parts relative to one another in the direction of the longitudinal axis of the telescoping column such that all stop means simultaneously take effect given complete extension and/or retraction of the telescoping column.

In the case of a stand wherein the inner of respectively three telescope parts adjacent to one another in the telescoping column is coupled to the outer telescope part by a tractor element, for example a cable, that is guided via a deflection roller attached to the middle telescope part such that the sections of the tractor element leading from the inner and the outer telescope part to the deflection roller proceed parallel to one another, it is provided in a modification of the invention that adjustment means are allocated to each of three telescope parts neighboring one another. The adjustment means can thereby be formed by means for modifying the length of the tractor element or by means for displacing one of the fastening points of the tractor element at the outer or inner telescope part in the direction of the longitudinal axis of the telescoping column. According to a preferred embodiment of the invention, however, it is provided that the adjustment means are respectively formed by means for displacing the deflection roller in the direction of the longitudinal axis of the telescoping column. This is advantageous because structural measures for fastening the deflection roller must be undertaken anyway and the adjustment means can thus be realized in a simple way. It is thus provided in a modification of the invention that the deflection roller is attached to a carrying part that is adjustably held at the central of three neighboring telescope parts with a set screw, whereby a compression spring can be arranged between the carrying part and the central telescope part in order to suppress play.

One embodiment of the invention provides that the stop means are attached such to the telescope parts that, when the telescoping column is completely retracted, those ends of all telescope parts facing toward the part of the x-ray examination apparatus lie in one plane. The assembly of the telescoping column turns out particularly simple as a consequence of this measure since the adjustment means must merely be actuated such for correct adjustment of the telescoping column that the said ends of the telescope parts lie in a common plane when the telescoping column is completely retracted.

BRIEF DESCRIPTION OF THE DRAWINGS

An exemplary embodiment of the invention is shown in the attached drawings. Shown are.

DESCRIPTION OF THE PREFERRED EMBODIMENTS

Figure 1:
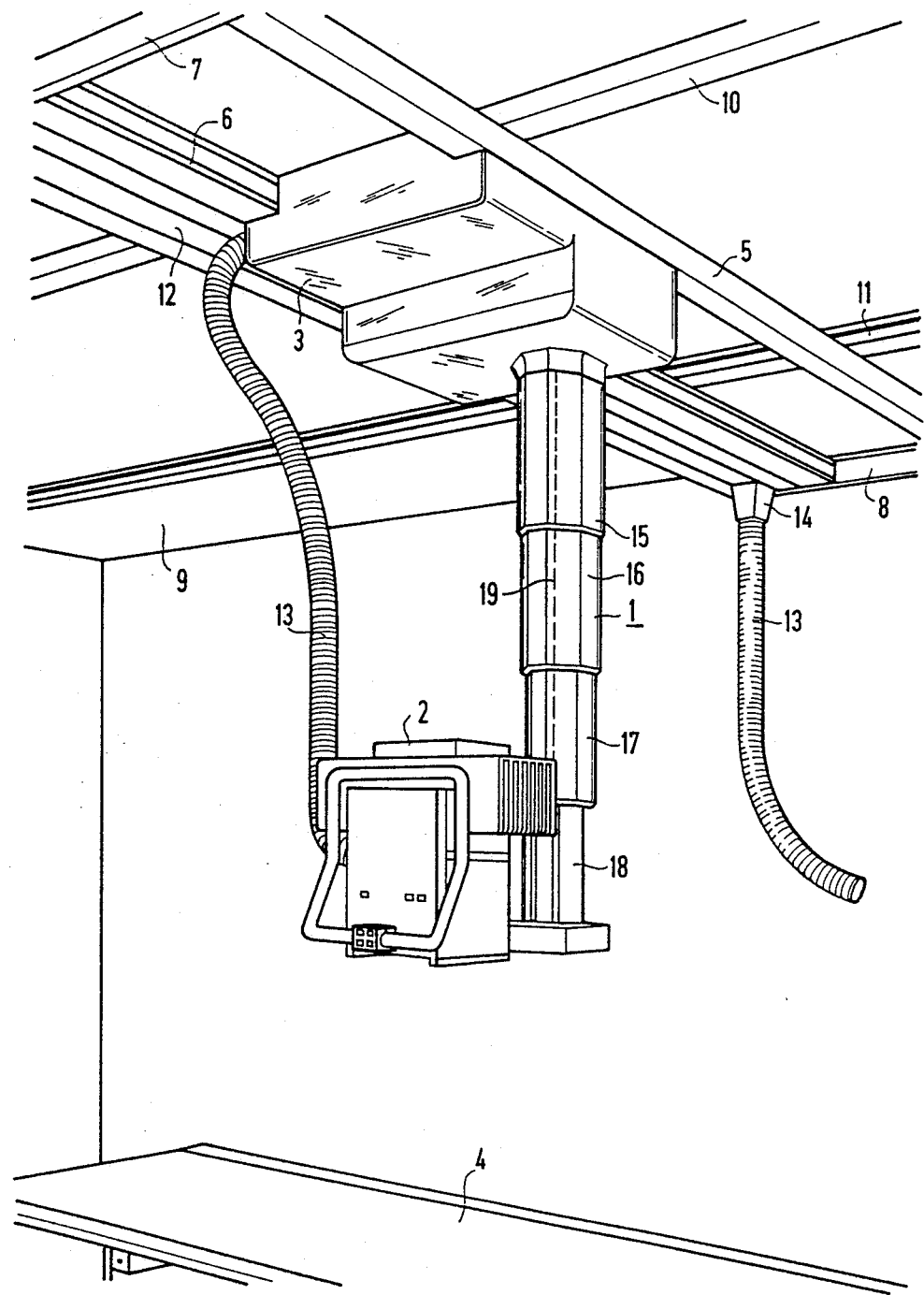
FIG. 1 is a perspective view of an inventive stand.

FIG. 1 shows a stand for an x-ray examination apparatus that is executed as a ceiling support comprising a vertical telescoping column 1 that guides a part of the x-ray examination apparatus, namely an x-radiator 2, in height-adjustable fashion. The telescoping column 2 is attached to a carriage above an examination table 4. The carriage 3 is displaceable in parallel rails 5, 6 with rollers (not visible), being displaceable transversely relative to the examination table 4. The rails 5 and 6 connected to one another with the end pieces 7 and 8 are in turn attached with rollers (not visible) displaceable in ceiling rails 10 and 11 attached to the ceiling of the examination room and proceeding parallel at a right angle relative to the rails 5 and 6, so that the x-radiator 2 is also displaceable along the examination table 4. A channel 12 in which a flexible supply cable 13 proceeds extends parallel to the rail 6, this supply cable 13 enters into the channel 12 through a cable bushing 14 provided in the region of the end piece 8 and stationary with reference to the carriage 3, emerges from this channel 12 in the region of the carriage 3 and is conducted to the x-radiator 2. The telescoping column 1 is composed of tubular telescope parts 15, 16, 17 and 18 joined inside of one another in a traditional way, whereby the telescope part 15 is rigidly attached to the carriage 3 and is thus stationary relative to the other telescope parts 16, 17 and 18 in the direction of the longitudinal axis of the telescoping column 2, whereas the telescope part 18 carries the x-radiator 2 and is also connected to the cable 19 entered with broken lines in FIG. 1 that can be rolled onto and off from a cable drum (not shown in the figure) for the height-adjustment of the x-radiator 2.

Figure 2:
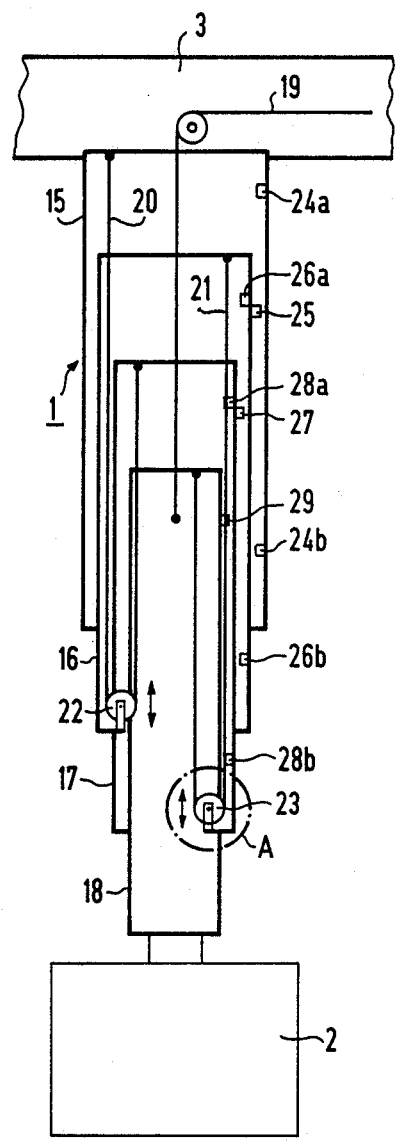
FIG. 2 is a schematic illustration of a longitudinal section through the telescoping column of the inventive stand.

As may be seen from FIG. 2, the telescoping parts 15, 16, 17 and 18 are coupled such to one another that, when the x-radiator 2 is adjusted with the cable 19, the respectively same relative displacement occurs between respectively two telescope parts 15 and 16, 16 and 17, 17 and 18 adjacent to one another. In detail, this is effected by tractor elements, namely by the cables 20 and 21, that couple the three telescope parts adjacent to one another, namely 15, 16 and 17 as well as 16, 17 and 18 to one another. The cables 20, 21 thereby have their ends respectively secured to the inner and outer telescope parts 17 and 15 or, respectively, 18 and 16 of three telescope parts 15, 16 and 17 or, respectively, 16, 17 and 18 that are adjacent to one another, being secured thereto in the region of their upper ends in FIG. 2. Deflection rollers 22 and 23 are respectively secured to the middle telescope parts 16 and 17, the cables 20 and 21 being respectively guided such over said deflection rollers 22 and 23 that the sections of the cables 20 and 21 respectively leading from the inside telescope part 17 or 18 to the outside telescope part 15 or 16 proceed parallel to one another.

Stops 24a, 24b and 25, 26a, 26b and 27, 28a, 28b and 29 are provided between telescope parts 15 and 16, 16 and 17, 17 and 18 neighboring one another, being provided for limiting the relative displacements occurring between these given complete extension or retraction of the telescoping column 1. The stops 24a, 26a and 28a are thereby respectively attached to the upper ends and the stops 24b, 26b and 28b are respectively attached to the lower ends of the inside walls of the telescope parts 15, 16 and 17 at equal distances from one another, whereas the stops 25, 27 and 29 are respectively provided at the outer walls of the telescope parts 16, 17 and 18 in the regions of the upper ends thereof.

Figure 3:
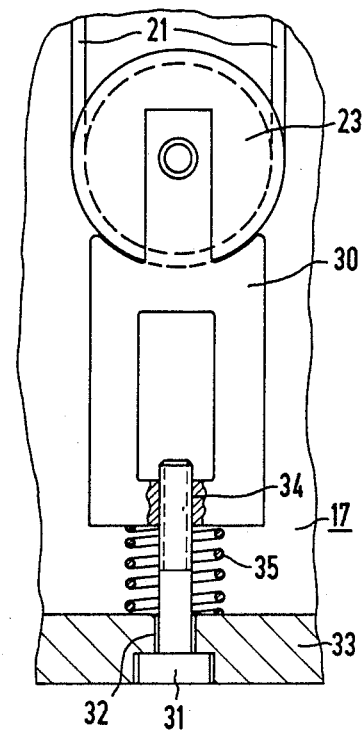
FIG. 3 is detail A of FIG. 2 in an enlarged illustration in comparison to FIG. 2.

In order to be able to assure that the stops 25, 27 and 29 engage essentially simultaneously with the stops 24b, 26b and 28b given complete extension of the telescoping column 1 and with the stops 24a, 26a and 26b given complete retraction of the telescoping column 1, this being required in order to keep inadmissible stresses away from the cables 20 and 21, respectively three telescope parts 15, 16 and 17 or, respectively, 16, 17 and 18 adjacent to one another have adjustment means allocated to them by means of which these are adjustable in position relative to one another in the way required for the simultaneous action of the stops. To this end, the deflection rollers 22 and 23 are attached to the telescope parts 16 and 17 adjustable in the direction of the longitudinal axis of the telescoping column 1, as symbolized in FIG. 2 by the double arrows allocated to the deflection rollers 22 and 23. In detail, as shown in FIG. 3 with reference to the example of the deflection roller 23 attached to the telescope part 17, the deflection rollers 22 and 23 are attached to a carrying part 30 that is held at the telescope part 17 in adjustable fashion with a set screw 31. The set screw 31 thereby extends through a through bore 32 that is provided in an edge 33 attached to that end of the telescope part 17 facing toward the x-radiator 2, i.e. to the lower end of the telescope part 17, extending through to the carrying part 31 that comprises a suitable threaded bore 34 for the set screw 31. Since a compression spring 35 is provided in order to avoid play between the carrying part 30 and the telescope part 17, the carrying part 30 can be adjusted in the direction of the longitudinal axis of the telescoping column 1 by turning the set screw 31. Since the set screw 31 belonging to the deflection roller 23 and the corresponding set screw of the deflection roller 23 are thus accessible without further ado even given a completely assembled telescoping column, the adjustment work at the deflection rollers 22 and 23 that is required in order to guarantee that the stops take effect simultaneously in the above-described way can ensue after assembly of the telescoping column 1 or of the entire stand has been carried out.

Figure 4:
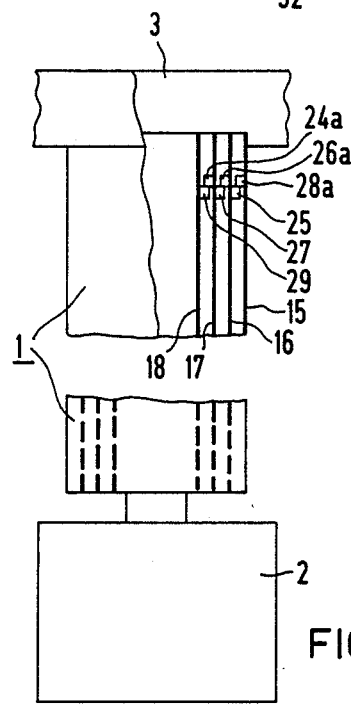
FIG. 4 is a partial longitudinal section through the telescoping column of the inventive stand in its completely retracted condition.

The required adjustment of the deflection rollers 22 and 23 is then managed in an especially simple way when the stops 24a, 26a, 28a and 25, 26, 27 are attached such to the telescope parts 15 through 18 that, when these stops take effect, i.e. given a completely retracted telescoping column 1, the ends of all telescope parts 15 through 18 facing toward the x-radiator 2 lie in a common plane, as indicated in FIG. 4, since the set screws merely have to be actuated such then that the ends of the telescope parts 15 through 18, as mentioned, are situated in a common plane. When, as mentioned above, the stops 24a and 24b, 26a and 26b, 28a and 28b at the telescope parts 15 through 17 each have the same spacing from one another, it is also guaranteed at the same time that the stops 24b and 25, 26b and 27, 28b and 29 simultaneously take effect given complete extension of the telescoping column 1.

As is apparent from the foregoing specification, the invention is susceptible of being embodied with various alterations and modifications which may differ particularly from those that have been described in the preceding specification and description. It should be understood that we wish to embody within the scope of the patent warranted hereon all such modifications as reasonably and properly come within the scope of our contribution to the art.

We claim as our invention:

1. A stand for an x-radiator, including a telescoping column that guides the x-radiator adjustable in the direction of the telescoping column of the longitudinal axisof the telescoping column, and which has at least three tubular telescope parts joined inside one another, whereof one is stationary relative to the others, one carries the x-radiator and one is connected to means for adjusting said x-radiator, the telescope parts being coupled to one another such that, when said x-radiator is adjusted, the same relative displacement occurs between each two telescope parts adjacent to one another, and respective stop means for limiting the relative displacement being provided between telescope parts adjacent to one another, comprising adjustment means for adjusting the positions of the telescope parts relative to one another when two or more stops means take effect at different times relative to each other, wherein the adjusting is in the direction of the longitudinal axis of the telescoping column such that all stop means essentially take effect simultaneously; said adjustment means being mounted so as to be actuatable without dismantling the telescoping column.

2. A stand according to claim 1, wherein said three tubular telescope parts comprise an inner telescope part, a middle telescope part and an outer telescope part and the inner telescope part is coupled to the outer telescope part by a tractor element that is guided over a deflection roller attached to the middle telescope part, being guided such that the sections of the tractor element leading from the inner to the outer telescope part proceed parallel to one another, and wherein said adjustment means are provided for said three telescope parts.

3. A stand according to claim 2, wherein the adjustment means are each comprise means for displacing the deflection roller in the direction of the longitudinal axis of the telescoping column.

4. A stand according to claim 3, wherein the deflection roller is arranged at an end of the middle telescope part that faces toward x-radiator.

5. A stand according to claim 3, wherein the deflection roller is attached to a carrying part that is held adjustable at the middle of three neighboring telescope parts, being held with a set screw.

6. A stand according to claim 5, wherein a compression spring is arranged between the carrying part and the middle telescope part in order to suppress play between the carrying part and the middle telescope part.

7. A stand according to claim 1, wherein the stop means are arranged such at the telescope parts that, given a completely retracted telescoping column, the ends of all telescope parts facing toward said x-radiator lie in a common plane when all stops are activated.

8. A stand for an x-radiator including a telescoping column that guides a part of the x-ray examination apparatus along a longitudinal axis, and which has at least three tubular telescope parts joined inside one another with respective stop means for limiting the relative displacement between telescope parts adjacent to one another, comprising:
  adjustment means for adjusting the positions of the telescope parts relative to one another when two or more stop means take effect at different times relative to each other, wherein the adjusting is in the direction of the longitudinal axis of the telescoping column such that all stop means essentially take effect simultaneously; said adjustment means being mounted so as to be actuatable from the exterior of the telescoping column without dismantling the telescoping column.

* * * * *